United States Patent [19]
Vincent

[11] Patent Number: 4,728,776
[45] Date of Patent: Mar. 1, 1988

[54] HEATED TRANSFER LINE FOR CAPILLARY TUBING

[75] Inventor: Kent D. Vincent, Cupertino, Calif.

[73] Assignee: Hewlett-Packard Company, Palo Alto, Calif.

[21] Appl. No.: 912,727

[22] Filed: Sep. 29, 1986

Related U.S. Application Data

[62] Division of Ser. No. 581,923, Feb. 21, 1984, Pat. No. 4,650,964.

[51] Int. Cl.$^4$ .............................................. F24H 1/10
[52] U.S. Cl. .................................................... 219/301
[58] Field of Search ............... 219/300, 301, 390, 535, 219/541

[56] References Cited

U.S. PATENT DOCUMENTS

| | | | |
|---|---|---|---|
| 1,727,585 | 10/1929 | Carleton | 219/300 |
| 2,489,753 | 11/1949 | Cox | 219/300 |
| 2,761,949 | 9/1956 | Colton | 219/300 |
| 3,766,357 | 10/1973 | Koester | 219/300 |

FOREIGN PATENT DOCUMENTS

| | | | |
|---|---|---|---|
| 1315187 | 12/1962 | France | 219/390 |
| 2361035 | 3/1978 | France | 219/390 |

*Primary Examiner*—Anthony Bartis
*Attorney, Agent, or Firm*—Jeffery B. Fromm

[57] ABSTRACT

A heated transfer line for heating a small glass capillary tube is disclosed. The transfer line is small and removable yet highly efficient, capable of uniformly heating a glass capillary tube over a 5-inch length to more than 400 degrees with less than 30 watts of power. The power is applied to an electrically conductive heater tube, which encircles the glass capillary, via first and second current conductors attached to respective ends of the heater tube. The first and second current conductors are arranged in proximity to the heater tube and back along the heater tube to a common point without touching each other. Electrical insulation is disposed between the heater tube and the first and second current conductors to electrically isolate the heater tube from the current conductors. A cover of thermal insulation is disposed over the heater tube and the current conductors and is used to thermally isolate the heater tube. An outer tube is disposed around the thermal insulation as a cover. A mounting ferrule is connected to the outer tube at the common point for mechanically mounting the transfer line and for providing an exit for the first and second current conductors.

7 Claims, 19 Drawing Figures

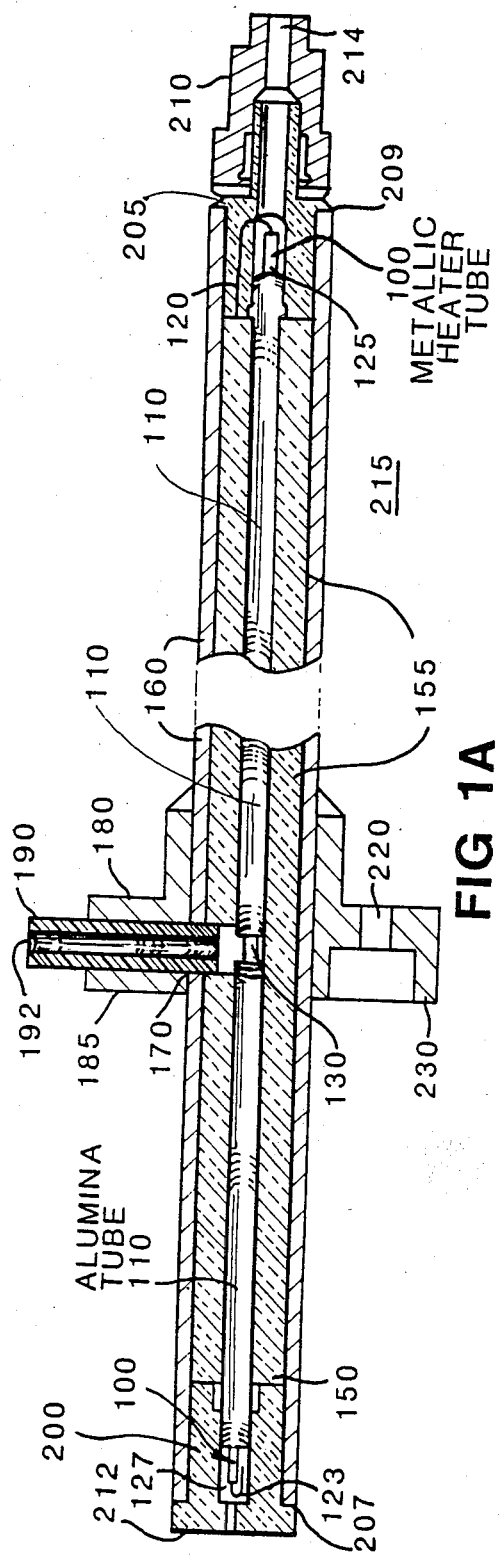
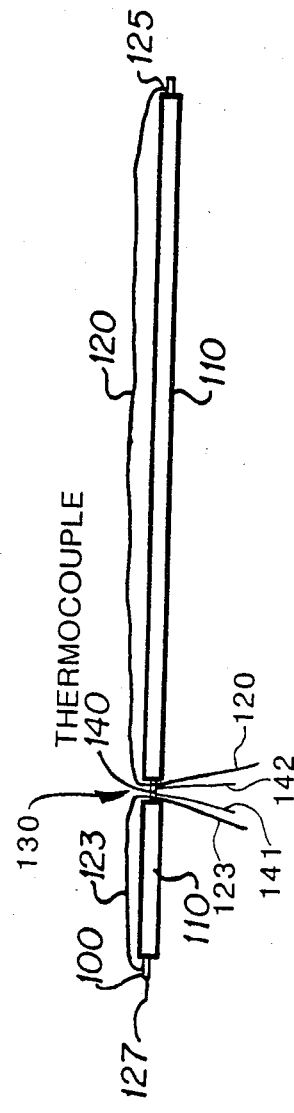
FIG 1A
FIG 1B

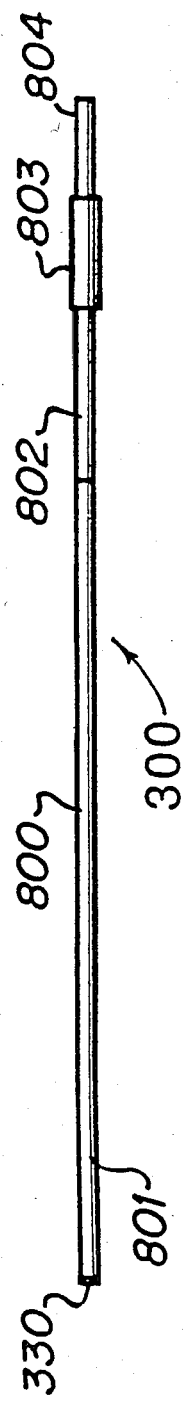
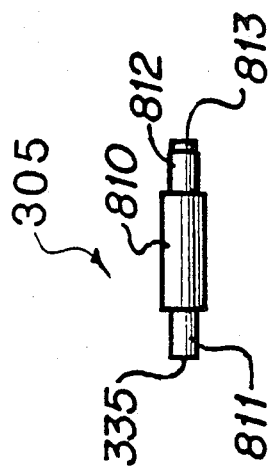
FIG 3A
FIG 3B

HEATED TRANSFER LINE FOR CAPILLARY TUBING

CROSS REFERENCE TO RELATED APPLICATION

This is a division of application Ser. No. 581,923, filed 2-21-84, now U.S. Pat. No. 4,650,964, granted Mar. 14, 1987.

BACKGROUND OF THE INVENTION

The general evolution of gas chromatographs has led to the use of very small glass capillary gas transfer lines and columns. A typical glass capillary tube has an inner diameter of 0.013 inch and 0.018 inch outer diameter. Vaporized chemical samples are carried, usually in a carrier gas, among the various devices in the gas chromatograph and between these devices and other devices located in adjacent detectors or other instruments external to the gas chromatograph through heated transfer lines.

The function of the transfer line heater is to maintain the vaporized chemical sample within defined temperature bounds as it is carried among the various components of the analytical instruments. A particular problem arises when the vaporized chemical samples are allowed to cool in the transfer lines, as this cooling can lead to precipitation of the sample out of the gas and onto the glass tube walls. Once this occurs, the chemical analysis is vitiated and there is the possibility that the glass tube can become plugged or that future chemical analysis can be contaminated. If heated above the temperature bounds, there is the possibility that the chemical sample will chemically react or decompose also vitiating the analysis. Therefore, it is important in gas chromatography that the glass capillary transfer lines be controllably heated.

Transfer lines are also used as gas conduits between analytical instruments, for example, between a gas chromatograph and a peripheral detector such as a spectrophotometer. For this use, the heated transfer line should be temperature controlled and powered in one instrument and protrude into the second. Since the small glass capillary tubes are difficult to clean in an instrument and are subject to breakage, the apparatus which heats the capillary tube must also permit its replacement.

In general, heated transfer lines are designed to operate in a temperature range of 150–350 degrees C., concurrent with that of present gas chromatographs. Since many chemical compounds have chemical reactivity or decomposition temperatures near their boiling points, it is highly desirable that the temperature range, or tolerance of the transfer lines be small, e.g. with 10 degrees C.

Several instrument oriented constraints on transfer line design have, heretofore, limited the temperature profile integrity of transfer lines. As a practical matter, it is desirable that a transfer line bridging two separate instruments be securely mounted, controlled and powered from one instrument while simply extending in to the second. The degree of mounting in the second instrument, if at all, may be determined by such influences as the need to isolate the instruments from vibration, or the need for instrument modularity. The external environment surrounding the transfer line as it extends from within one instrument to within another can vary significantly. For example, a transfer line traversing from the inside of a heated gas chromatograph oven, through the oven wall insulation and out to the ambient air gap between instruments experiences a variation in temperatures ranging from perhaps 20 to 350 degrees C.

Prior art transfer lines have been limited to the rather simple approach of inserting the gas capillary tube in comparatively large body of a highly thermal conductive metal housing which is heated by an enclosed heater, such as a cartridge or band heater. This combination is further surrounded by a thermal insulator of some type, which tends to mitigate changes in the surrounding environment. The larger the metal body and insulation, the more uniform the temperature. Several disadvantages are evident in this approach. First, since the mass of the metal housing is primarily designed to house the heater rather than the small glass tube, such heated transfer devices are particularly power inefficient and subject to substantial heat loss in the surrounding instrument. Analytical detectors such as spectrophotometers are particularly sensitive to temperature gradients due to the precise alignment of their optics and can not afford the heat dissipation from a relatively large transfer line operating at 350–400 degrees C., as is required in gas chromatography. Typically, these prior art transfer lines have diameters of 5 cm or more and due to their size, dissipate as much as several hundred watts of power into their host instruments. These large diameters also inhibit coupling of the transfer line to instrument devices. It is not uncommon for cold junctions to develop at the coupling which are 50 degrees C. or more below the desired operating point.

Alternatively, prior art transfer lines have consisted of a weave of highly electrically resistant wire, such as an alloy of 80% nickel and 20% chromium, and fibrous glass or ceramic insulation wound about the glass capillary tube into which the glass capillary may be inserted. Electrical current supplied to the metal wire heats the capillary. Although usually smaller in diameter than the previously described transfer lines, the woven transfer lines lack temperature uniformity when positioned in a temperature environment which changes along the length of the transfer line. This is because there is insufficient thermal conductivity in the axial direction of the capillary tube.

Other prior art transfer lines have consisted of a tubular structure heated at one end, the capillary tube passing through the center of the tube. The heating element is housed in metal attached to the tube and heat is transferred by conduction down the length of the tube. Although this approach provides for a smaller size on the non-heated end, it obviously suffers from non-uniform heating of the capillary tube. To maintain a minimum temperature at the cold end the heater must be brought to a higher temperature than required for the chemical analysis.

SUMMARY OF THE INVENTION

In summary, the invention embraces an apparatus which permits gases to be transferred from one device to another through a glass capillary tube with minimal changes of temperature. The apparatus consists of a heated transfer line and an optional oven feedthrough.

The heated transfer line works by transferring the heat, which is generated when an electrical current is passed through a highly resistive metal tube, to a glass capillary tube, which is inserted into the metal tube.

The heated transfer line is small in size and low in power dissipation when compared to the prior art. The heater consists of several concentric tubes, each with a special purpose. The heater tube through which current passes is small in diameter and only slightly larger than the glass capillary tube and is designed to efficiently transfer the heat directly to the capillary tube. The heater tube is electrically insulated, except for the ends where power is supplied through two electrical conduits or wires. These conduits form the second layer of the transfer line and also generate heat as a current passes through them. The conduit tubes are specially shaped in order to generate more heat at the ends, without raising temperatures significantly in the middle of the tube. Their length together is approximately equal the length of the heater tube and permits power to be supplied at a central location near the middle of the tube. At this juncture, a thermocouple is mounted which is used to monitor the transfer line temperature. The conduit tubes are covered with a thermal insulator and the entire assembly is enclosed within an outer tube.

The oven feedthrough consists of a short piece of copper pipe mounted to a thermal insulator with a hole in the center through which a heated transfer line, similar to the one described above, may pass. The insulator serves to insulate the copper pipe and heated transfer line from the oven. The inner diameter of the copper pipe is several times larger than the transfer line which because of its thermal conductivity attempts to keep a constant temperature over its length thereby providing a more gradual change in temperature between the oven and the ambient air for the heated transfer line.

The invention is superior to the prior art in several ways. The invention provides considerably more uniform temperature throughout the transfer line than the prior art. The invention dissipates low power, typically 8 watts compared to several hundred watts of the prior art. The invention is small in size, the transfer line heater being 0.25 inches in diameter rather than the 2 to 5 inches or greater typically of the prior art.

DESCRIPTION OF THE DRAWINGS

FIGS. 1A, 1C and 1D illustrate sectional, side and end views respectively, of a heated transfer line for capillary tubing according to a first embodiment of the present invention.

FIG. 1B shows a portion of the heated transfer line shown in FIGS. 1A, 1C and 1D.

FIGS. 3A and 3B illustrate the variations in thickness of the conduit tube walls used to selectively heat the transfer line of FIGS. 2A-2D.

DESCRIPTION OF THE PREFERRED EMBODIMENT

The heater tube is conveniently selected from hypodermic needle syringe stock, usually hardened stainless steel. The small size of the glass capillary diameter allows the use of small diameter syringe stock with thin walls, both combining to provide smallness of size and an electrical resistance favorable towards its use as a heating element. The small size of the heater tube and its concentric location about the glass capillary results in a small uniform transfer line heater configuration for a glass capillary which is removable. Likewise, with this configuration power consumption is greatly reduced due to the small exposed transfer line surface area required at any given temperature.

In order to supply a current to the heater tube, the heater tube is first electrically insulated over its external surface, then electrical wires, or other electrical conduits, are connected to the uninsulated ends of the heater tube and made to extend back over the length of the insulated heater tube to some centrally located mutual point along its length from which general electrical connection of the heated transfer tube unit can be made externally. A temperature sensor is also coupled to the heater tube, and the leads of the sensor are also brought out at the centrally located mutual point.

Figure 1D:
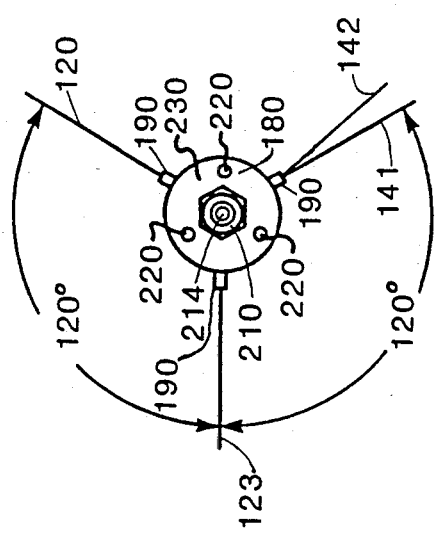

A first embodiment of the invention is shown in FIGS. 1A, 1B, 1C and 1D. A heater tube 100 made of fully hardened stainless steel or a high resistance nickel/chromium alloy tubing having a 0.031 inch outer diameter and a 0.020 inch inner diameter is inserted into an alumina tube 110 having an outer diameter of 0.062 inch and inner diameter of 0.032 inch as shown in FIG. 1A. The heater tube 100 extends out beyond the alumina tube 110 0.09 inch on each end. Copper wires 120 and 123 of 28 gauge size are wrapped about and silver soldered to the exposed ends 125 and 127 of the heater tube 100 and each wire 120 and 123 is brought to an intermediately located ferrule position 130 as shown in FIG. 1B. A thermocouple 140 is cemented with a high temperature ceramic cement on the outer surface of the alumina tube 110 at the ferrule position 130. Lengths of a center drilled ceramic fiber tube insulation 150 and 155 having an outer diameter of 0.210 inch and inner diameter of 0.062 inch are slid over and abutted to the alimina tube 110 and over the 28 gauge copper wires 120 and 123. Yet another tube 160, a stainless steel sheath having outer diameter 0.250 inch and inner diameter 0.210 inch, as shown in FIG. 1A is slid over the assembly of FIG. 1B. The thermocouple 140 and copper wires 120 and 123 are pulled out through the fiber tube insulation 150 and 155 and through holes 170 drilled raidally in the tube 160 at 120 degrees radial spacing. A stainless steel ferrule 180 shown in FIG. 1A is slid over the tube 160 and positioned with the wires 120 and 123 and the leads 141 and 142 of thermocouple 140 entering 120 degrees spaced grooves 185 in the ferrule 180. The leads 120, 123, 141, and 142 are ceramic cemented in place and exit through 0.032 inch inner diameter, 0.062 inch outer diameter alumina tube 190 via holes 192. The ferrule 180 is silver soldered to the tube 160. Alumina end caps 200 and 205 are cemented with a high temperature alumina cement to each end 207 and 209 of the tube 160. Onto end cap 205 is cemented a stainless steel fitting 210 having a thread. The fitting 210 and end caps 200 and 205 each has a central hole passing therethrough so that a glass capillary tube (not shown) can enter through either end 212 or 214 of the thus formed heated transfer line 215 shown fully assembled in FIG. 1C and pass out the other end. Holes 220 located radially about the flange 230 of the ferrule 180 as shown in FIG. 1D allowed the mounting of the heated transfer line 215 to a flat surface.

Figure 1C:
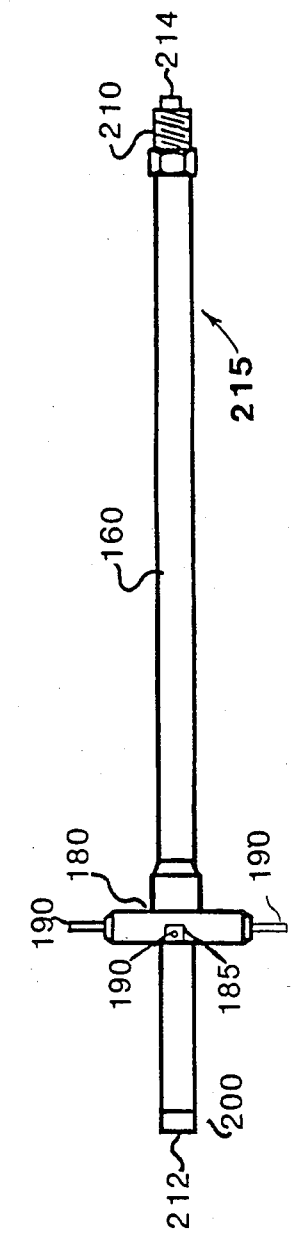

In operation the transfer line 215 of FIG. 1C is powered by passing current through the copper wires 120 and 123 which thus allows current to flow uniformly through the entire length of heater tube 100. The power dissipated in the heater tube 100 causes its rapid heating. The surrounding ceramic fiber insulation 150 and 155 restricts heat loss while the ceramic tube 110 and ceramic end caps 200 and 205 isolate the heater tube 100 electrically from the tube 160 exterior and the copper wires 120 and 123.

The above described heated transfer line has a temperature capability in excess of 400 degrees C. However, the metal ferrule 180 serves as an undesired heat sink creating a localized lower temperature in the heater tube 100 at the ferrule location 130. In addition, the construction is labor intensive.

Figure 2A:
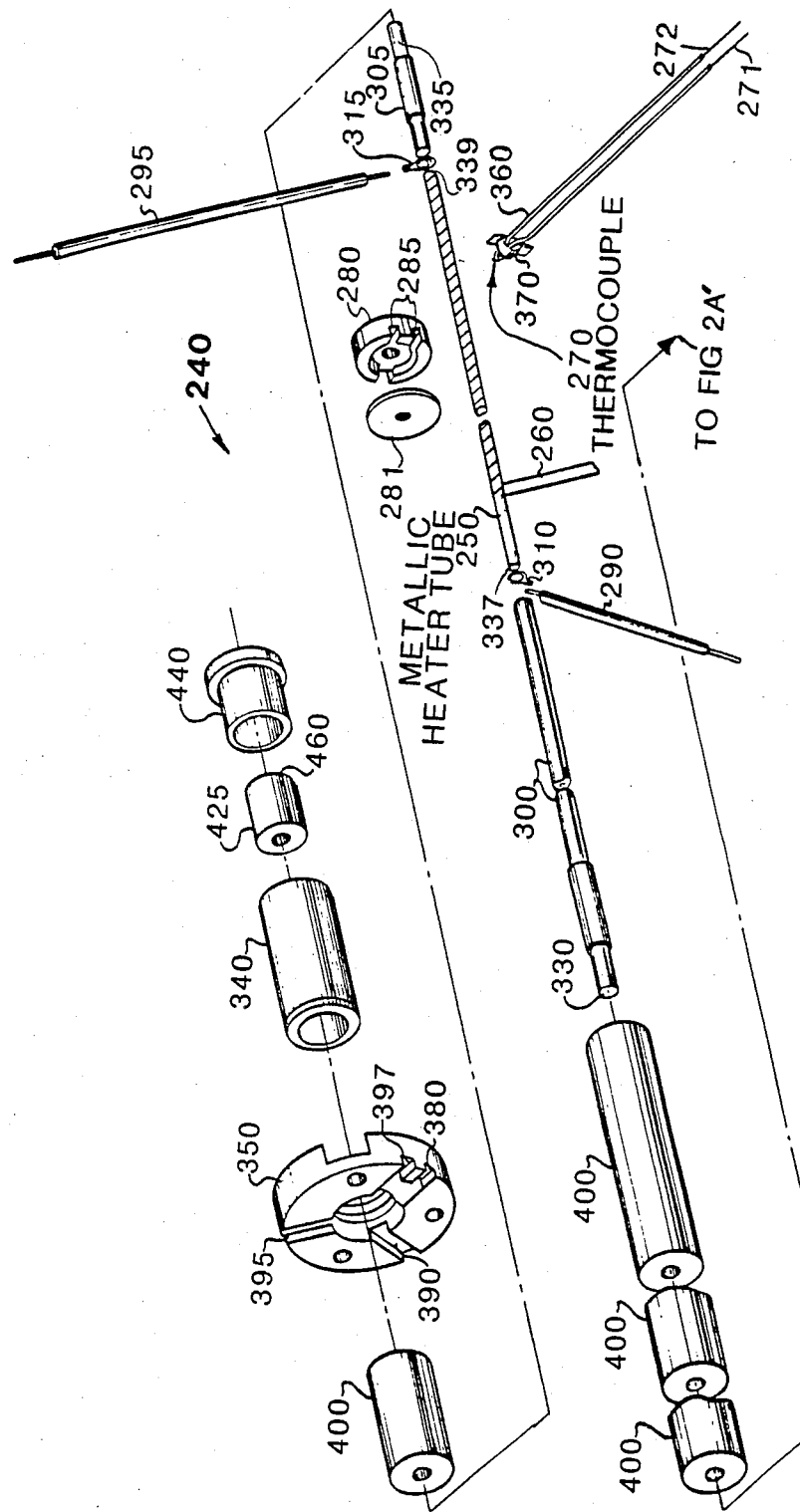
FIGS. 2A, and 2A' illustrate exploded portions of a heated transfer line for capillary tubing according to a second embodiment of the present invention.
Figure 2A:
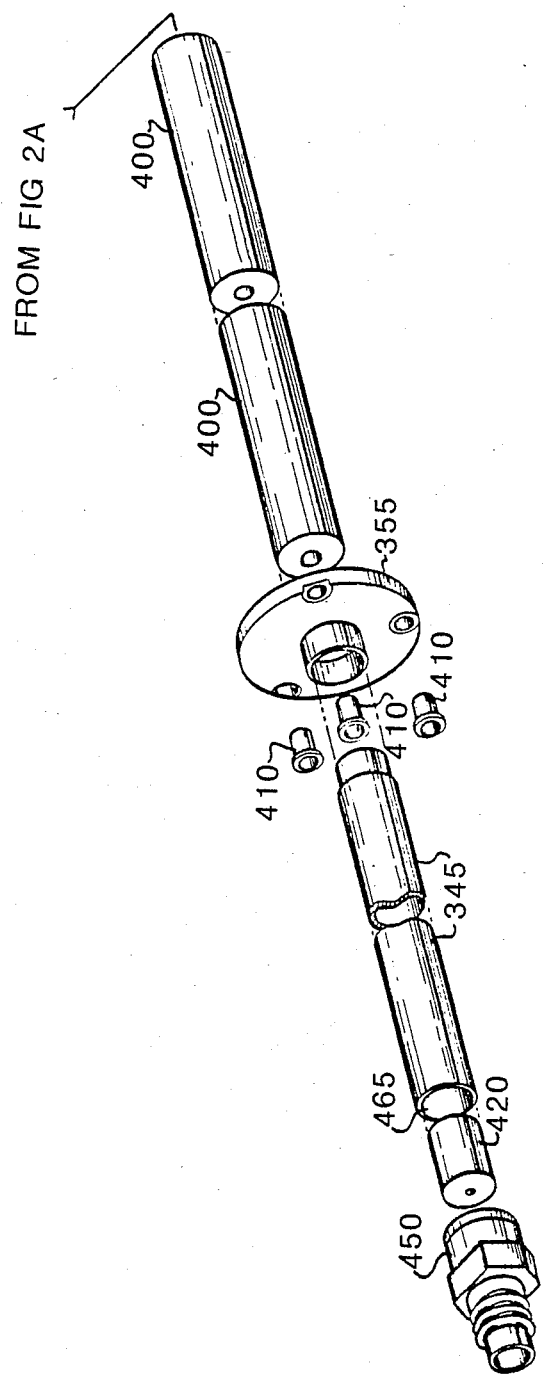

A second and preferred embodiment shown in FIGS. 2A, 2A', 2B, 2B', and 2C is now disclosed to overcome these difficulties while maintain both the function and size of the first embodiment. A fully hardened stainless steel or high resistance nickel/chromium alloy tube 250 having a 0.031 inch outer diameter, 0.023 inch inner diameter and 5.676 inch length is wrapped with a 0.062 inch wide by 0.001 inch thick polyimide insulation tape 260 about the heater tube 250 periphery and along its length to within about 0.25 inch of the end of tube 250 as shown in FIG. 2A. A 0.001 to 0.0015 inch thick silicon based adhesive on one side of the insulation tape 260 allows adhesiion between the tube 250 and tape 260. The adhesive is only needed during assembly, and actually evaporates during use.

Figure 4A:
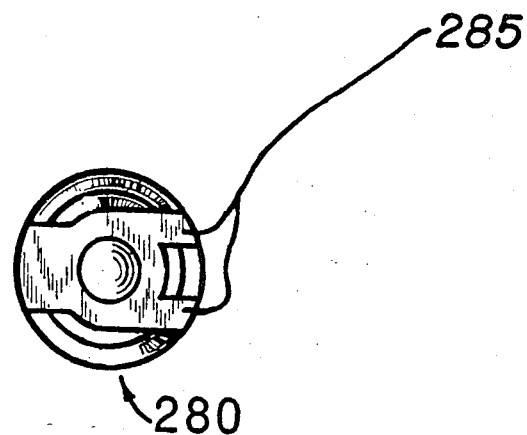
FIGS. 4A, 4B and 4C illustrate left, front, and right side views, respectively, of a capture ring for use with the heated transfer line of FIGS. 2A-2D.
Figure 4B:
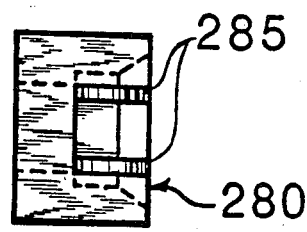
Figure 4C:
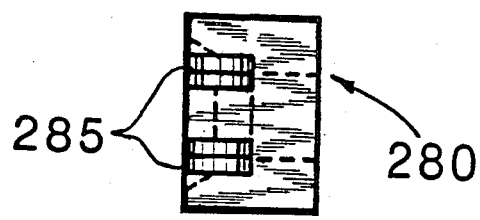

A thermocouple 270 having 0.010 inch diameter leads 271 and 272 is positioned on the tape 260 on tube 250 approximately 0.5 inch from one end of tube 250. The thermocouple 270 and both of its leads 271 and 272 are held in place over opposing sides of the insulated heater tube by sliding the capture ring 280 over the thermocouple 270, and covering the open end of the capture ring 280 with the polyimide (e.g., Vespel available from DuPont Corporation) washer 281 thereby trapping the thermocouple against the insulated heater tube and between the washer 281 and the capture ring 280. Top, left side and right side views of capture ring 280 are shown in FIGS. 4A, 4B, and 4C respectively and thermocouple leads 271 and 272 will exit through slots 285 in capture ring 280. A typical capture ring 280 will have the following dimensions:

- d1 = 0.094 inches in diameter
- d2 = 0.018 inches
- d3 = 0.015 inches
- d4 = 0.059 inches in diameter (centerbore)
- d5 = 0.035 inches
- d6 = 0.038 inches
- d7 = 0.064 inches
- d8 = 0.034 inches
- d9 = 0.034 inches. The function of capture ring 280, in addition to positioning and holding thermocouple 270 directly against the tape 260, is to position the leads 271 and 272 of the thermocouple 270 and to electrically isolate them from each other, and to thermally insulate the heater tube 250 from its surroundings.

Figure 5A:
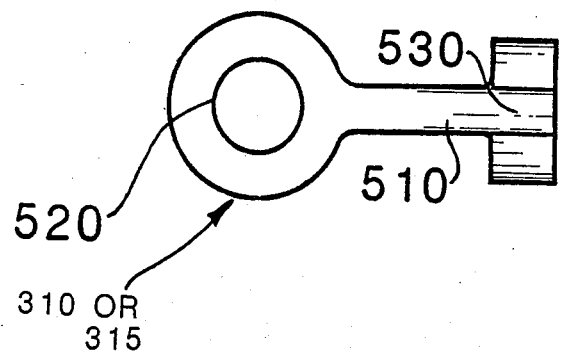
FIGS. 5A, 5B and 5C illustrate top, side and perspective views, respectively, of the solder lug used to connect an electric conductor to the conduit tubes.
Figure 5B:
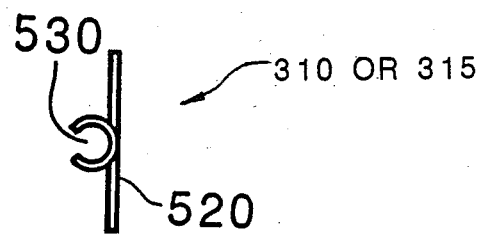
Figure 5C:
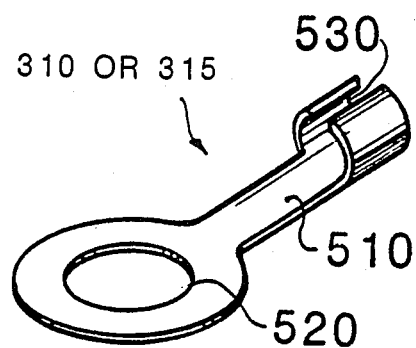
Figure 6:
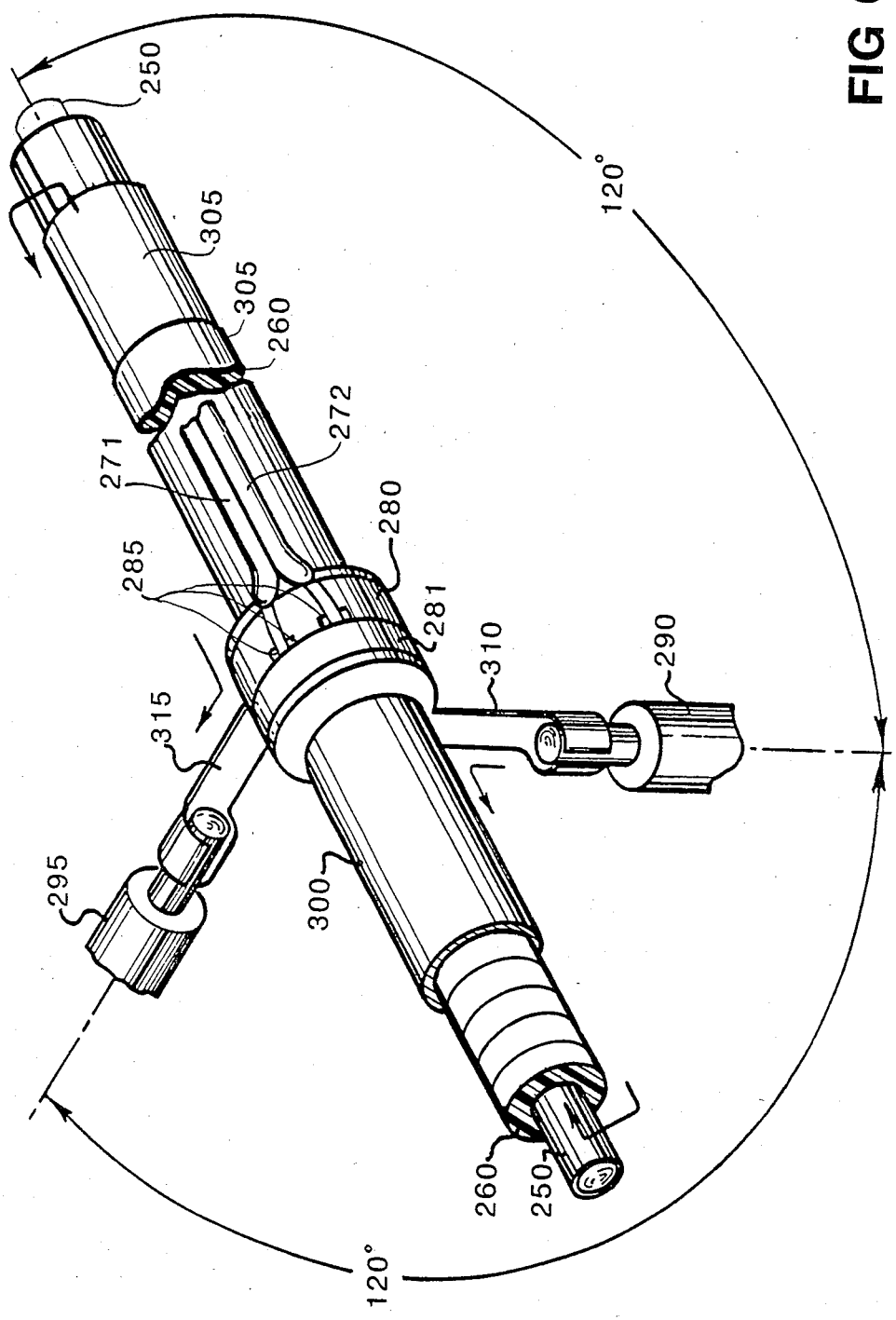
FIG. 6 illustrates an assembled view of a portion of the heated transfer line of FIGS. 2A-2D.
Figure 2C:
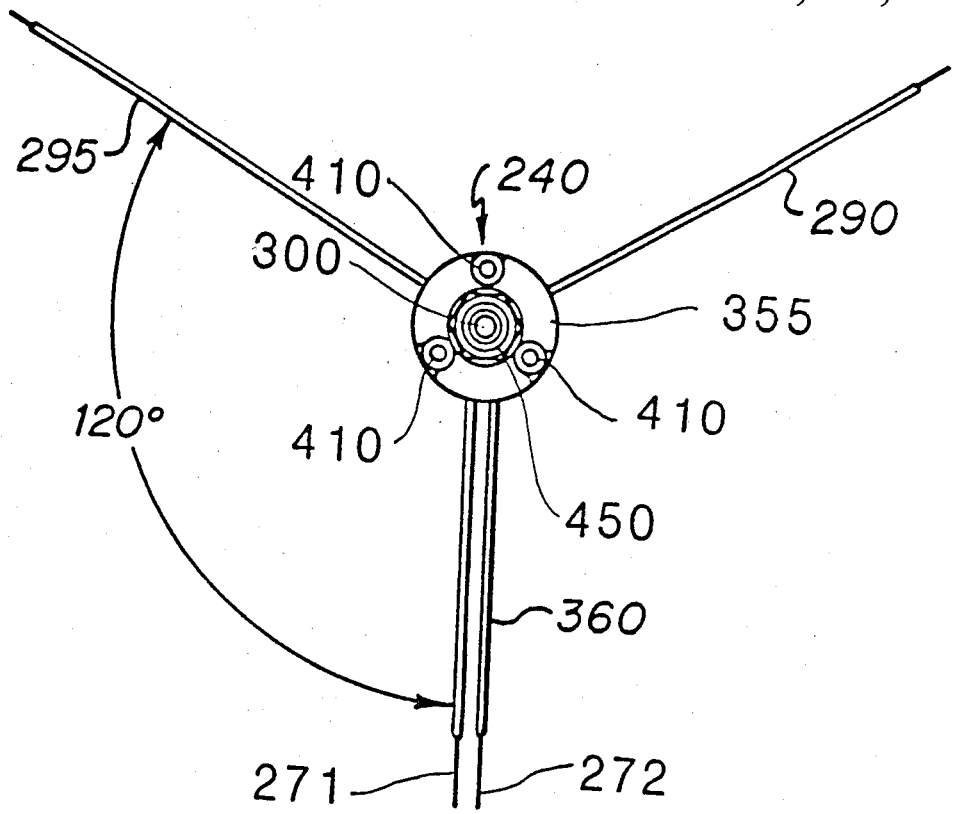

Electric current is supplied to the heated transfer line through lead wires 290 and 295. Typically, wires 290 and 295 are 22 gage single strand silver plated copper wires insulated with Teflon. Electrical lead wires 290 and 295 are connected to the two respective solder lugs 310 and 315 by crimping and silver soldering the respective joints. Because the power required to heat the transfer line is quite small, a very small increase in power or the addition of a relatively small heat loss can drastically affect the local temperature of the transfer line. Therefore, the goal of the connector design is to provide a good electrical connection which is thermally invisible to the heater and conduit tubes. Since the connector would normally conduct heat away from the heater tube, this may be accomplished by passing a current through the connector which must heat the connector such that its temperature and thermal conductivity combine to provide an apparent thermal resistance which matches that of the insulation which surrounds the heater and conduit tube. FIGS. 5, 5B and 5C illustrate solder lugs 310 or 315 whose dimensions meet the above conditions by use of a precisely dimensioned ribbon 510 between the connecting points 520 and 530. A typical solder lug 310 or 315 will have the following dimensions:

- f1 = 0.090 inches in diameter
- f2 = 0.052 inches in diameter
- f3 = 0.070 inches
- f4 = 0.022 inches
- f5 = 0.010 inches in radius
- f6 = 0.125 inches
- f7 = 0.200 inches
- f8 = 0.030 inches
- f9 = 0.0050 inches. The two solder lugs 310 and 315 are then attached to the ends of their respective conduit tubes 300 and 305. Silver soldering is chosen to restrict high temperature corrosion at the electrical crimp. Conduit tubes 300 305 are typically stainless steel tubes having an outer diameter of 0.072 inch and inner diameter 0.040 inch. Once the solder lugs 310 and 315 are attached, conduit tubes 300 and 305 are slid over heater tube 250 oriented with the solder lugs at 120 degrees as shown in FIG. 6. With this orientation, the unattached ends 330 and 335 of conduit tube 300 and 305 are silver soldered to the exposed ends 337 and 339 of heater tube 250. The insulation tape 260 serves to electrically insulate heater tube 250 from conduit tubes 300 and 305 such that current will be allowed to travel down the conduit tubes 300 and to the silver solder joint 330, then through the heater tube 250 to the solder joint 335 and back out through tube 305. FIG. 6 illustrates the partially assembled transfer line where the solder lugs 310 and 315 and thermocouple mounting hardware meet.

Short and long outer tubes 340 and 345, respectively are inserted into ferrules 350 and 355, respectively as shown in FIGS. 2A and 2A' and staked into place. Staking occurs by flaring out the exposed end of each tube into the respective ferrules to prevent removal. Ferrules 350 adn 355 are constructed from polyimide for purposes of temperature resistance and to further restrict the flow of heat out of the assembled transfer line heater 240 shown in FIGS. 2B and 2B'. Teflon flex tubing 360 is inserted over each lead 271 and 272 of thermocouple 270 and crimped in place with crimp 370. During assembly, crimp 370 fits into an enclosed cavity 380 in ferrule 350 such that the flex tubing 360 is not easily pulled out of the assembled transfer line heater 240. Each ferrule 350 and 355 with tube 340 and 345 is slid over their respective ends 335 and 330 of the previous assembly, as shown in FIG. 2A. Each wire 290 and 295 and the leads 271 and 272 of thermocouple 270 are positioned respectively in grooves 390, 395, and 397 in upper ferrule 350. Ceramic fiber insulating tubes 400 are slid over the ends 335 and 330 of the above assembly in the annulus formed between the electrical conduits 305 and 300 and the outer sheathes 340 and 345. The insulation tubes 400 are pushed down against capture ring 280 and cover 281 and fit snugly adjacent to each other. The outer most insulating tube 400 is trimmed to allow the total proper length of insulation. Ferrules 350 and 355 are then riveted together with eyelets 410. The center holes of eyelets 410 serve as holes for mounting of transfer line heater 240. Polyimide insulators 420 and 425 are slid and positioned over the ends 335 and 330 of conduits 300 and 305. Insulators 420 and 425 serve to electrically insulate the conduits 300 and 305 from the outer tubes 345 and 340. End caps 440 and fitting 450 are made of stainless steel and are dipped in liquid nitrogen then quickly tapped into their respective ends 460 and 465 of the outer tubes 340 and 345. The expansion fit forms an interfering fit when the end cap 440 and fitting 450 are warmed to room temperature in the outer tubes 340 and 345.

A uniform tube generates uniform temperature rise along its length when an electric current is passed through the tube. A temperature profile of an operating uniform tube reveals however an uneven temperature profile due to uneven heat transfer to the environment. This problem is particularly severe toward the ends of the tube. As a major improvement of the present heated transfer line, its uniform temperature is accomplished by varying the wall thickness of the conduit tubes along the length of the transfer line heater. At any given position along said length the total power per segment is equal to the power losses of the heater tube and the power losses of the surrounding conduit tube. Since the current I is identical for each segment the power input per segment, q, is:

$$q = I^2(Rht + Rct) \quad <1>$$

Where Rht and Rct are the electrical resistances of the heater and conduit tubes respectively. The power loss from the heater tube to the environment varies along the length of the tube, for example, the end losses are greater than losses at the center of the transfer line. Therefore in order to keep a uniform temperature, it is desirable to add additional power to those segments with greater losses. Referring to equation 1, this can be accomplished by locally increasing the electrical resistance in those segments with greater losses. The resistance in a given segment may be increased by adjusting the wall thickness of any of the heating tubes. Since in the preferred embodiment the heater tube has assumed a minimal practical size for the overall resistance of the transfer line, a wall thickness adjustment is most easily made by altering the outer diameter of the conduit tubes.

This effect can be expressed mathematically in simple form by noting the electrical circuit analogy to the field of thermodynamics. The heater tube temperature To is related to the ambient temperature Ta, the power input per segment q and the thermal resistance between To and Ta of Rth by the equation:

$$To = qRth + Ta$$

$$To = I^2(Rht = Rct)Rth + Ta \quad <2>$$

At the transfer line midpoint the thermal resistance Rth consists primarily of a sum of series resistances for a thermal dissipation path which extends radially out from the heater tube. Moving toward the ends, a parallel resistance enters into Rth due to axial losses (assuming the ends are cooler). This effectively lowers Rth, consequently lowering To for a constant electric current I. As Rth varies, the electrical resistance of the conduit tube, Rct, can be varied to compensate by altering preferably the outer radius of the conduit tube at the affected section. For a tube the electrical resistance can be calculated as:

$$Rt = \frac{pL}{pi(do^2 - di^2)/4} \quad <3>$$

where p is the resistivity of the tube material at the operating temperature To, L is the evaluated tube length, pi is 3.14 . . . , and do and di are the outer and inner tube diameters, respectively.

Thermal resistance can be calculated in simple configuration but may be more complex when all parameters are not known. The temperature distribution along a transfer line can easily be measured, however, by inserting a 0.010 inch diameter thermocouple probe into the end of a glass capillary and traversing the assembly down the length of the heater tube when operating.

Assuming the following values:
Rht: do=0.031" di=0.023" p=3.8386e-5 ohm-inch
Rct: do=0.063" di=0.038" p=3.8386e-5 ohm-inch
Ta=25 degrees C. and To=300 degrees C.
and, due to practical grinding restrictions, a minimum outer diameter do=0.050", then applying the above formulas 2 and 3 it may be shown that a temperature rise of 45 degrees C. is possible. In the preferred embodiment an even larger tube was used to obtain an even higher temp rise.

This analysis works well as a first order approximation, although an exact solution is not achieved since an adjusted segment is affected by adjoining unadjusted segments and due to changes in Rth which are temperature dependent.

FIG. 3A, which is a picture of conduit tube 300 having an overall length of 5.236 inches, shows the various reductions in diameter for a particular application of the preferred embodiment. At point 803, 0.450 inches of length of the tube diameter (0.072 inches) is unchanged. The tube diameter is ground down 0.009" in sections 802 (0.750 inches long) and 804 (0.450 inches long) and further ground to 0.053" in section 800, and still further ground to an outer diameter of 0.050" for a length of 0.020 inches at point 801. FIG. 3B shows the similar grinding on conduit tube 305 having an overall length of 0.540 inches. The tube diameter (0.072 inches) is not ground at 810 for a length of 0.250 inches, it is ground down 0.009" at 811 (for a length of 0.140 inches) or 812 (for a length of 0.061 inches) and still further ground to 0.50" at section 813 (for a length of 0.089 inches).

Figure 2B:
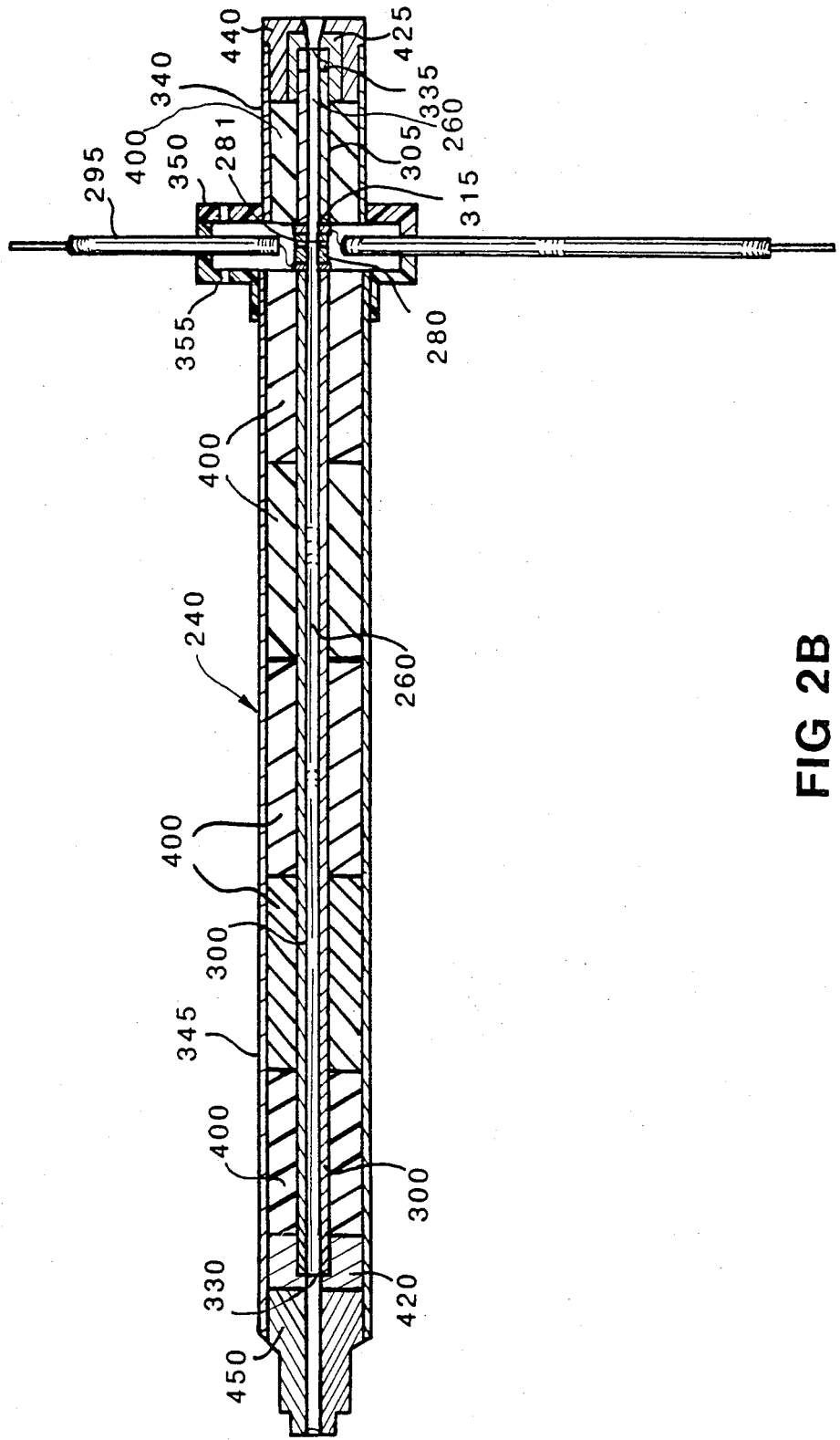
FIGS. 2B, 2B' and 2C illustrate sectional and end views, respectively, of the heated transfer line shown in FIGS. 2A and 2A'.
Figure 2B:
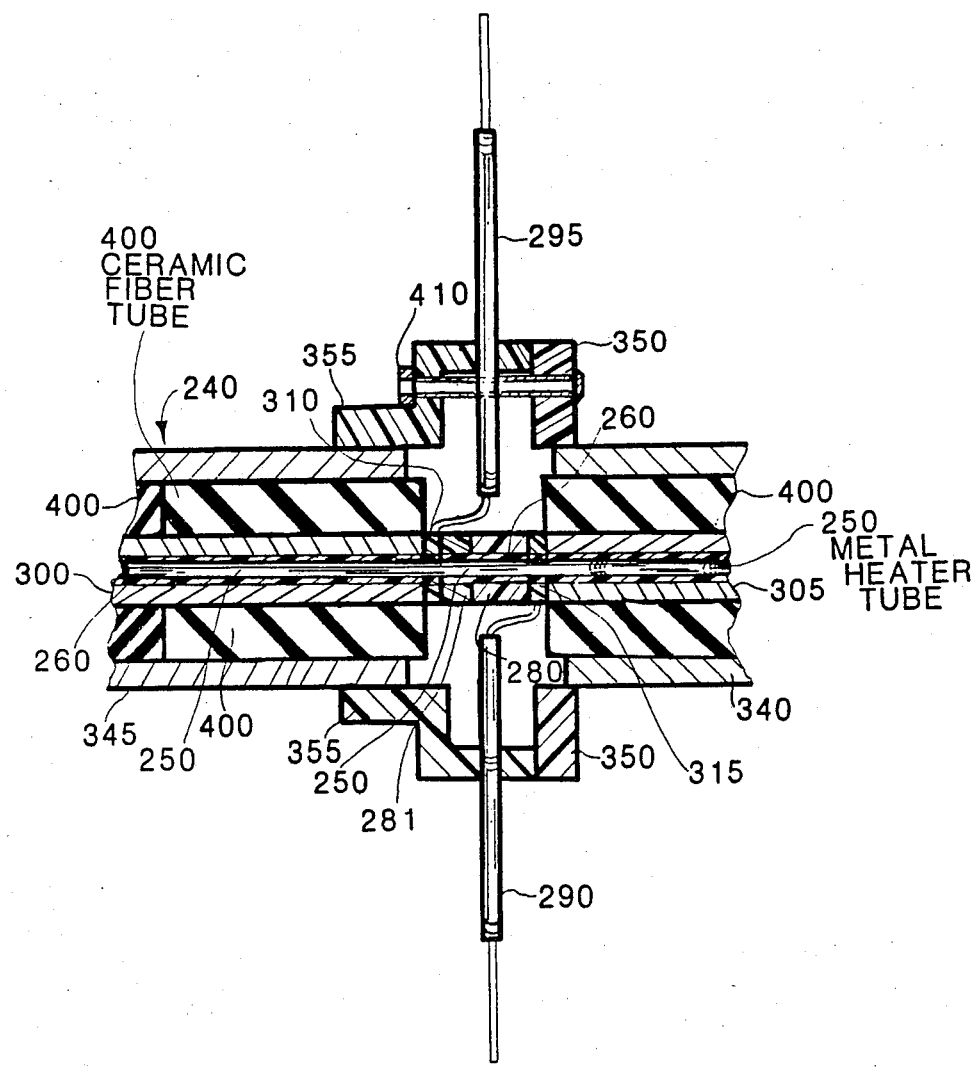

The second embodiment of the transfer line heater 240 as shown in FIGS. 2B, 2B' and 2C achieves uniform heating to 400 degrees C. with less than 10 watts of dissipated power with a variation of less than 10 degrees C.

Figure 7:
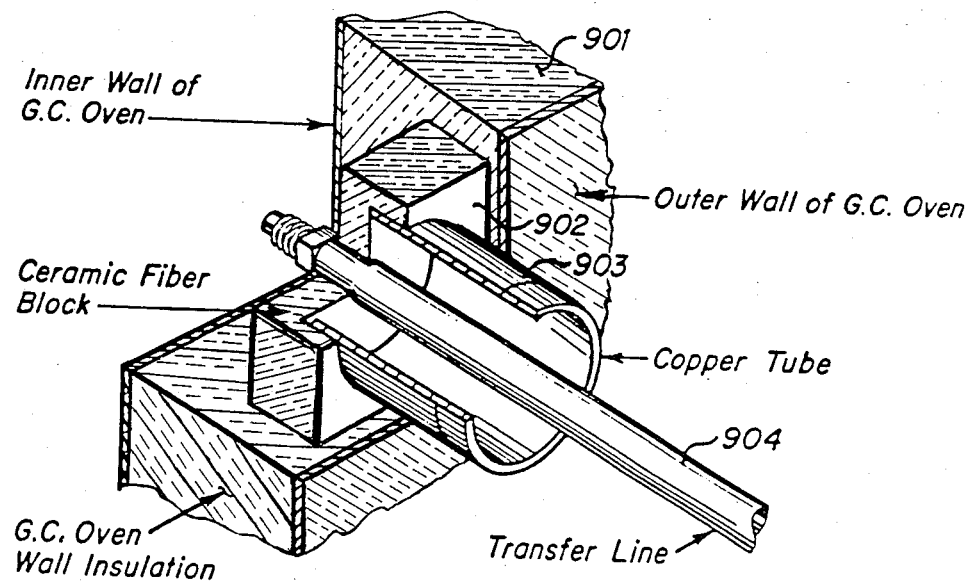
FIG. 7 is an illustration in cross section of an oven feedthrough.

Apparent variations in the external temperature environment of the transfer line when mounted in various gas chromatograph oven configurations has also led to a need to improve the method of connecting the transfer line to the oven while minimizing gas chromatograph thermo-mechanical differences in transfer line performance. An additional feedthrough device for this purpose is shown in FIG. 7. The feedthrough consists primarily of a copper tube 903 whose internal diameter is substantially larger than the transfer line heater's outer diameter. The copper tube mounted in the gas chromatograph oven wall insulation 901 strives to be at constant temperature along its length. The copper tube is purposefully oversized to allow sufficient thermal grounding of the tube to the ambient to reduce the variations in temperature of the tube along its length, and also, to allow for variations in oven wall thickness among the various gas chromatograph instruments.

To reduce the thermal sink effect of the copper tube on the oven itself, the copper tube is not allowed to protrude through to the oven interior, but instead extends into a refractory ceramic fiber block 902 containing a centrally located hole to allow the axial passage of the heated transfer line 904 into the oven. The block also serves to isolate the heated transfer line from exposure to the high temperature oven and to prevent convection flow out of the oven and over the transfer line. Use of the oven feedthrough permits a heated transfer line with less than a plus or minus 10 degress C. variation when used with a gas chromatograph.

I claim:

1. An apparatus for heating a length of tubing to a uniform temperature with an electric current, the apparatus comprising:
    a heater tube which is electrically conductive and has first and second ends;
    first insulating means substantially covering the length of the heater tube for electrically insulating the heater tube;
    first and second electrically conductive conduit tubes having a combined length substantially equal to the length of the heater tube, said first and second conduit tubes covering the first insulating means and each having an outer end electrically connected, respectively to the first and second heater tube ends, the opposite inner ends of the conduit tubes coming into closely spaced proximity at a common point along the heater tube;
    first and second conductor means electrically connected to the first and second conduit tube inner ends near said common point for supplying electric current to said heater tube through said first and second conduit tube;
    second insulating means surrounding and thermally insulating the first and second conduit tubes;
    first and second outer tubes substantially covering the second insulating means and having first and second outer tube ends with the opposite inner ends of the outer tubes coming into closely spaced proximity at said common point along the heater tube; and
    mounting means connected to the outer tube inner ends in a mounting plane which passes through said common point along the heater tube mechanically mounting the apparatus and providing an exit for the first and second conductor means.

2. An apparatus as in claim 1 wherein the heater tube is composed substantially of a high resistance nickel/chromium alloy.

3. An apparatus as in claim 1 wherein the first and second conduit tubes are composed substantially of a stainless steel.

4. An apparatus as in claim 1 wherein each of the first and second conduit tubes are composed of a tube with at least one predetermined variation in tube wall thickness.

5. An apparatus as in claim 1 wherein the thermal resistances of both conductor means are approximately equal to the thermal resistance of the second insulating means.

6. An apparatus as in claim 1 further comprising a temperature sensor thermally connected to the heater tube and having leads exiting the appartus substantially in the mounting plane.

7. An apparatus as in claim 1 further comprising first and second tube fittings connected to the first and second outer tube ends.

* * * * *